(12) United States Patent
Adamson

(10) Patent No.: US 10,580,134 B2
(45) Date of Patent: Mar. 3, 2020

(54) METHOD FOR MEASURING A DENTAL OBJECT

(71) Applicant: DENTSPLY SIRONA Inc., York, PA (US)

(72) Inventor: Anders Adamson, Darmstadt (DE)

(73) Assignee: DENTSPLY SIRONA INC., York, PA (US)

(*) Notice: Subject to any disclaimer, the term of this patent is extended or adjusted under 35 U.S.C. 154(b) by 0 days.

(21) Appl. No.: 16/406,310

(22) Filed: May 8, 2019

(65) Prior Publication Data

US 2020/0005454 A1    Jan. 2, 2020

Related U.S. Application Data

(62) Division of application No. 14/421,299, filed as application No. PCT/EP2013/066994 on Aug. 14, 2013, now Pat. No. 10,325,365.

(30) Foreign Application Priority Data

Aug. 14, 2012    (DE) .................... 10 2012 214 473

(51) Int. Cl.
*G06T 7/00*    (2017.01)
*G01B 21/04*    (2006.01)
(Continued)

(52) U.S. Cl.
CPC ........ *G06T 7/0012* (2013.01); *A61B 1/00009* (2013.01); *A61B 1/00055* (2013.01);
(Continued)

(58) Field of Classification Search
CPC ......... G06T 7/0012; G06T 2207/30036; A61B 5/7405; A61B 1/00009; A61B 1/247;
(Continued)

(56) References Cited

U.S. PATENT DOCUMENTS 7,349,104 B2 *   3/2008  Geng ................... A61B 5/1077
                                                356/603
2001/0014171 A1 *  8/2001  Iijima ....................... G06T 7/55
                                                382/154
(Continued)

*Primary Examiner* — James M Pontius
(74) *Attorney, Agent, or Firm* — Dentsply Sirona Inc.

(57) ABSTRACT

A method of imaging a dental object using a dental camera comprising the steps of: recording a plurality of three-dimensional optical images of a dental object using a dental camera; determining whether an overlapping area, formed by at least a partial overlap of the plurality of three-dimensional optical images, satisfies one or more recording requirements; and generating an acoustic sound during the recording using a sound generator; wherein the sound serves as a feedback for the user and imparts to the user information (i) about the current status of a recording of the images and/or (ii) about recording requirements of the dental camera; wherein a speed of movement of the dental camera relative to the object is determined by (i) using a motion sensor on the dental camera or (ii) by analysis of the measured images; and wherein the acoustic sound is generated as a function of the determined speed of movement.

3 Claims, 3 Drawing Sheets

(51) Int. Cl.
- *A61B 5/107* (2006.01)
- *A61B 5/00* (2006.01)
- *A61C 9/00* (2006.01)
- *H04N 7/18* (2006.01)
- *H04N 13/204* (2018.01)
- *A61B 1/247* (2006.01)
- *A61B 1/00* (2006.01)
- *G01B 11/25* (2006.01)

(52) U.S. Cl.
CPC ............ *A61B 1/247* (2013.01); *A61B 5/1077* (2013.01); *A61B 5/1079* (2013.01); *A61B 5/4547* (2013.01); *A61B 5/7405* (2013.01); *A61C 9/006* (2013.01); *A61C 9/0053* (2013.01); *G01B 11/25* (2013.01); *G01B 21/047* (2013.01); *H04N 7/18* (2013.01); *H04N 13/204* (2018.05); *F04C 2270/0421* (2013.01); *G01B 2210/52* (2013.01); *G06T 2207/30036* (2013.01)

(58) Field of Classification Search
CPC . A61B 5/1079; A61B 1/00055; A61B 5/1077; A61B 5/4547; A61C 9/006; A61C 9/0053; H04N 7/18; H04N 13/204; G01B 11/25; G01B 2210/52; G01B 21/047; F04C 2270/0421
See application file for complete search history.

(56) References Cited

U.S. PATENT DOCUMENTS

2016/0014396 A1* 1/2016 Glinec ................ A61C 9/0053
433/29
2017/0056136 A1* 3/2017 Adamson ............ A61C 9/0053

* cited by examiner

METHOD FOR MEASURING A DENTAL OBJECT

CROSS-REFERENCE TO RELATED APPLICATIONS

This is a divisional application of U.S. Non-Provisional application Ser. No. 14/421,299, filed on Feb. 12, 2015, which is a national phase application of International Application No. PCT/EP2013/066994, filed Aug. 14, 2013, which claims the benefit of and priority to German Application No. 102012214473.0, filed on Aug. 14, 2012, which is herein incorporated by reference for all purposes.

TECHNICAL FIELD

The invention relates to a method for measuring a dental object using a dental camera, wherein several optical three-dimensional images of the object are produced during the measurement.

PRIOR ART

Several methods and dental cameras for optical measurement of a dental object are known from the prior art.

DE 10 2006 009 177 A1 discloses a dental handpiece, in particular a camera handpiece. An image is recorded by operating a piezo film. Recording of an image can be triggered by an acoustic signal by means of an acoustic display device. No exact details are disclosed about the design of the acoustic display device, as well as the type of acoustic signal.

In addition, DE 10 2008 024 817 A1 discloses a camera handpiece which generates a tactile alarm for the user when an image is triggered. The tactile alarm is generated by a tactile display device, comprising a piezo oscillator or a magnetic oscillator.

The user can obtain a feedback about the status of the measurement and/or about the specific recording requirements, such as adequate focusing or successful recording, only by using a visual display device, such as a monitor.

A disadvantage of the aforementioned dental cameras and methods is in the fact that, during the measurement, the user must repeatedly look at a monitor of the dental object in order to obtain a feedback about the current status or the recording requirements. This can lead to a longer measurement time.

The object of the present invention is thus to provide a measurement method, which allows simple and reliable monitoring of the measurement process.

DESCRIPTION OF THE INVENTION

The invention relates to a method for measuring a dental object using a dental camera, wherein several optical three-dimensional images of the object are produced during the measurement. During the measurement, an acoustic sound is generated by means of a sound generator. This sound serves as a feedback for the user and imparts to the user information about the current status of a recording of the images and/or about specific recording requirements of the dental camera. During the optical measurement, several three-dimensional optical images of the dental object are recorded and then combined to form a global image. After each individual image, a check is performed automatically using a computer to ascertain whether an overlapping area between the images to be joined meets specific recording requirements for correct recording. The sound is generated by the sound generator if the recording requirements for the checked image are met. Alternatively, the sound can be generated if the recording requirements for the checked image are no longer met. The recording requirements include an adequate size of the overlapping area, an adequate waviness of the object surface in the overlapping area, an adequate roughness of the surface in the overlapping area, an adequate number of characteristic geometries in the overlapping area, an adequate number of measuring points in the overlapping area and/or an adequate image quality of the image in the overlapping area.

For example, the ICP recording method (iterative closest point algorithm) may be used as the recording method. This algorithm is a known method for recording two-dimensional and/or three-dimensional objects. The purpose of this method is to map two different 3D models of an object approximately accurately onto one another. For this purpose, different rotations and translations onto corresponding point pairs of the two 3D models are used. A square error of the distances between the point pairs is thereby minimized. In detail, the nearest neighbors of a certain point are determined in the first step. In the next step, the transformation is calculated for the recording. As a result, the calculated transformation is applied to the point pairs to be recorded. This iterative approximation is performed until the two 3D models correspond in the overlapping area.

Alternatively or in addition, the recording can also take place on the basis of the color of the recorded object, the surface curvature of the recorded object or on the basis of geometric correspondences. When recording on the basis of geometric correspondences, a pattern recognition algorithm is used, in which the second image is searched for a certain geometric pattern, such as an occlusal surface of a certain tooth, from the first image.

The recording requirements are not fulfilled, for example, if the dental camera is moved too rapidly in relation to the object and therefore the size of the overlapping area is not adequate. Another reason might be that the autofocus of the dental camera has a blurred setting and therefore the object mapped is out of focus, so that the image quality of the respective image is insufficient. Another reason might be that movable objects such as the patient's tongue or the attending dentist's finger are detected during the measurement. As a result, the overlapping areas of the image do not correspond. Another reason for a flawed recording might be that the lens of the dental camera fogs over because of the high moisture level in the patient's mouth and therefore the image quality is inferior. The aforementioned reasons could thus result in failure to fulfill the recording requirements defined in advance. In such a case, the sound may then be generated as a signal tone to inform the user of a flawed recording. Alternatively, a certain sound may also be generated for each successful recording. In another alternative, a first sound may be generated for a successful recording and a second sound, which is distinctly different from the first sound, may be generated for a flawed recording.

Therefore, a flawed recording is prevented between the images to be combined. A reliable recording is made possible by the adequate brightness and roughness of the surface of the overlapping area, in contrast with a flat surface. The adequate number and arrangement of the characteristic geometries, such as fissures or tooth stumps, for example, also enable a reliable recording. If there is an adequate image quality, the dental object is imaged sharply and with a high contrast. A reason for low contrast might be inadequate illumination of the object, for example. A reason for a blurred image might be a faulty autofocus setting, for example. An adequate number of measuring points in the overlapping area is also necessary for a successful mission. In other words, the sound is generated as a signal tone for a flawed recording only when the number of measuring points in the transition area is lower than a defined limit value.

The optical images are measured using the dental camera, which can function according to a strip projection method, for example. In a strip projection method, a pattern of multiple parallel strips is projected onto the object to be measured, and then a three-dimensional image of the object is produced on the basis of the distortion of these strips using a triangulation method.

Alternatively, the optical measurement may be performed by using a dental camera, which is based on a confocal optical method or on a color strip projection method.

In the color strip projection method, a pattern of several color strips is projected onto the object. Then the depth coordinates for the measuring points are determined and a 3D model of the object is created. The color strips can then be identified unambiguously on the basis of their color. For example, four color strips and/or three color transitions may be used for the color coding of the color strips. The color strips can be created by means of a slide, for example.

The strip width for such strip projection methods may be 130 µm in the measurement volume on the object to be measured, for example.

For the optical measurement, a different strip projection method in which the strips are coded using different light properties such as intensity, color, polarization, coherence, phase, contrast, location or running time is used.

A so-called confocal chromatic triangulation method, which combines the concepts of a confocal measurement and a triangulation method, may also be used for the measurement. The fundamental idea is that the surface of an object is colored in such a way that the height coordinate can be inferred directly from the color. The colors are created by spectral splitting of the projected light, wherein each wavelength is focused on a separate height coordinate.

During the measurement, the handheld dental camera is moved relative to the dental object, such as a lower jaw or an upper jaw, the three-dimensional optical images being created at regular intervals. The individual images can be created at a clock frequency between 10 Hz and 20 Hz, for example. Next, the individual images can be recorded by computer and combined to form a global image.

The sound generator may be a loudspeaker, which is integrated into the dental camera. The created acoustic sound may be designed of any type in its duration, in its tone pitch and/or its volume. The sound may be designed, for example, as a signal tone for exceeding defined recording requirements, e.g., for an inferior contrast of the respective image or being out of focus. The sound may also be a signal tone for a flawed recording of the combined images.

An advantage of this method is that the user receives information acoustically directly via the sound thereby generated, the current status of the recording and/or specific recording requirements of the dental camera. It is therefore no longer necessary for the user, such as a dentist, to glance repeatedly at a monitor during the measurement in order to observe specific recording requirements or the status of the recording.

An object distance of the object to be measured may advantageously be determined relative to the dental camera, wherein the sound is generated as a function of this object distance.

The object distance can be determined on the basis of the three-dimensional images. In creating the three-dimensional images, several measuring points are detected on the object surface and the 3D coordinates are calculated. Thus also the distance between the camera and the respective measuring points is known. The distances between the respective measuring points within a defined object section are averaged in determining the object distance. For example, the distances may be averaged only for those measuring points located on a defined occlusal surface of a certain tooth.

As a refinement, an occlusal surface may also be subdivided into multiple sectors, wherein one point of emphasis is formed for each sector, and only the distances between the camera and the respective points of emphasis of the sectors are averaged. The object distance can thus be calculated directly for each individual three-dimensional image.

Alternatively, the distance measuring unit can measure the distance between the dental camera and the object, for example, using an ultrasonic transit time method, also known as a sonar method. An ultrasound is generated by the distance measuring unit, reflected by the object and measured by a sensor in the distance measuring unit. Then the distance to the object can be calculated on the basis of the measured transit time of the ultrasound. The advantage of this method is that the distance can be measured very rapidly without requiring a trial focusing or contrast measurement.

An advantage is that on the basis of the object distance, a focal distance between a focal point of an object surface of the object to be measured and a focal plane of the dental camera can be determined, wherein the sound is generated as a function of this focal distance.

With the strip projection methods and confocal methods that are used, the emitted light is focused on a certain focal plane and/or on a sharp layer, which is defined by the settings of the focusing lens in the dental camera. The distance between the focal plane and the dental camera is thus known and can be calculated according to a pinhole camera model. Therefore, the focal distance between the focal plane and the focal point of the object surface can be calculated by subtracting the object distance from the distance of the focal plane relative to the dental camera.

Within a measuring field, the distance to the focal plane can be varied slightly, so that the mean distance to the focal plane within the measuring field can be used as a relevant measured variable for the sound generation.

Advantageously, the generated sound can be a modulated sound and be changed depending on focal distance between the object surface and the focus plane of the dental camera in its tone pitch and/or its volume.

The modulated sound might be a dissonant sound, for example, that indicates the focal distance by means of the tone pitch and/or by means of the volume.

The sound may advantageously be a short clicking sound, which is generated as soon as defined limits of a sharp focus range of the dental camera are exceeded.

The limits of a sharp focal range may amount to +5 mm and −5 mm relative to the focal plane, for example.

Another method according to the invention relates to a method for measuring a dental object using a dental camera, wherein several optical three-dimensional images of the object are produced during the measurement. An acoustic sound is generated by a sound generator during the measurement. The sound serves as a feedback for the user and imparts to the user information about the current status of a recording of the images and/or about specific recording requirements of the dental camera. A speed of movement of the dental camera relative to the object is determined by using a motion sensor on the dental camera or by analysis of the measured images, wherein the sound is generated depending on the detected speed of motion.

The optical images are measured by means of the dental camera which can function according to a strip projection method, for example. In a strip projection method, a pattern of multiple parallel strips is projected onto the object to be measured, and, on the basis of the distortion of these strips, a three-dimensional recording of the object is generated by using a triangulation method.

Alternatively, the optical measurement may be performed by using a dental camera, which is based on a confocal optical method or a color strip projection method.

In the color strip projection method, a pattern of multiple color strips is projected onto the object. Then the depth coordinates for the measuring points are determined and a 3D model of the object is generated. The color strips can be identified unambiguously on the basis of their color. For the color coding of the color strips, for example, four color strips and/or three color transitions may be used. The color strips can be generated, for example, by means of a slide.

The strip width for such strip projection methods may amount to 130 µm, for example, in the measurement volume on the object to be measured.

It is also possible to use another strip projection method for the optical measurement, in which the strips are coded using different light properties such as intensity, color, polarization, coherence, phase, contrast, location or transit time.

A so-called confocal chromatic triangulation method may also be used for the measurement, wherein the concepts of a confocal measurement and a triangulation method are combined. The fundamental idea then consists of the fact that the surface of an object is colored, so that it is possible to directly infer a height coordinate from a color. The colors are produced by a spectral splitting of the projected light, focusing each wavelength on a separate height coordinate.

During the measurement, the handheld dental camera is moved relative to the dental object such as a lower jaw or an upper jaw, wherein the three-dimensional optical images are generated at regular intervals. The individual images can be generated at a clock frequency between 10 Hz and 20 Hz, for example. Next, the individual images can be recorded by computer and combined to form a global image.

The sound generator may be a loudspeaker, which is integrated into the dental camera. The generated acoustic sound may be designed in any way with regard to its duration, its tone pitch and/or its volume. The sound may be designed as a signal tone, for example, for exceeding specific recording requirements, such as an inferior contrast or the respective image being out of focus. The sound may also be a signal tone for a flawed recording of the images to be combined.

The motion sensor may be integrated into the dental camera and can determine the relative speed of movement of the dental camera relative to the object. However, the relative speed of movement can also be determined by the analysis of the measured images, wherein the speed of movement is determined on the basis of an offset of the object in successive images and on the basis of the known interval of time between the images.

As an alternative, the speed of movement can be determined by analysis of the measured images. For example, the ICP method may be used for this. In this method, the relative transformations of the measured object in the individual images recorded in succession are calculated. These transformations may represent shifts in and rotations of the object. With knowledge of the image frequency and the determined transformations, the speed of movement can be determined for individual measuring points on the object. An average speed of movement within a measuring field may be used as a measured variable for the sound generation. Therefore, the speeds of movement of the individual measuring points occurring with a rotation of the camera within the measuring field are averaged out. The measuring field may have a size of 17 mm×14 mm, for example.

An advantage of this method is that the user receives information about the current status of the recording and/or about specific recording requirements of the dental camera directly acoustically by means of the generated sound. It is therefore no longer necessary for the user or the dentist to glance repeatedly at a monitor during the measurement in order to observe specific recording requirements or the status of the recording.

The sound generator may advantageously emit a modulated sound, wherein the tone pitch and/or the volume of the sound can be changed depending on the speed of movement of the dental camera relative to the object.

The modulated sound in this way indicates the relative speed of movement by means of the tone pitch and/or the volume.

The generated sound may advantageously be a short clicking sound, which is generated as soon as a defined critical speed of movement is exceeded.

The user is therefore pointed out by such a signal tone that the critical speed of movement has been exceeded.

The critical speed of movement may amount to 2 cm/second, for example.

DRAWINGS

Brief Description of the Drawings

The invention will now be explained on the basis of the drawings which illustrate.

DESCRIPTION

Exemplary Embodiment

Figure 1:
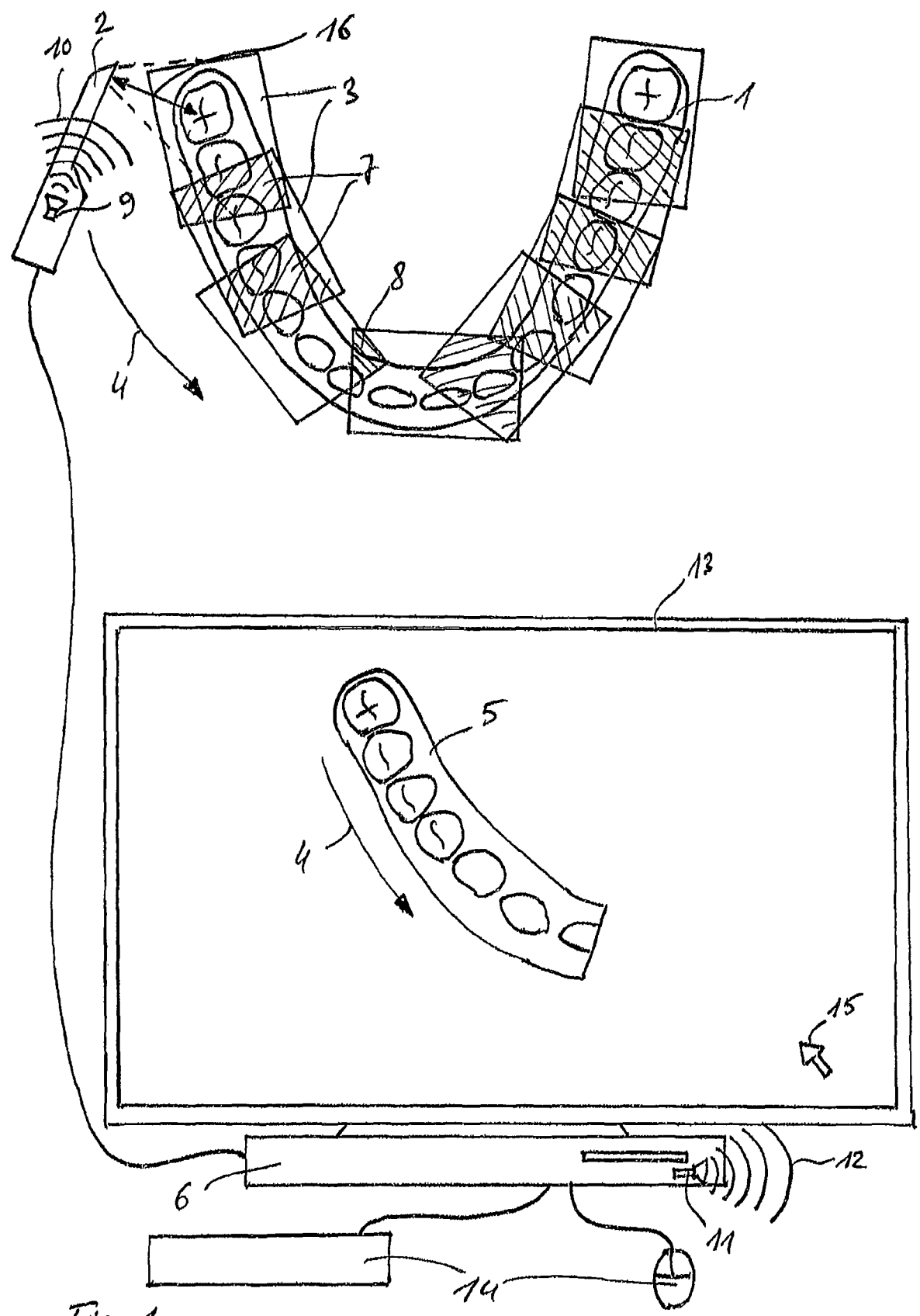
FIG. 1 a diagram illustrating the present method for measuring a dental object.

FIG. 1 illustrates a diagram for clarification the present method for measuring a dental object 1, i.e., a lower jaw, using a dental camera 2, wherein several individual optical three-dimensional images 3 are produced during the measurement. The three-dimensional images 3, which are represented in the form of rectangles, are measured by using the dental camera 2, which is moved along a measurement path 4 relative to the object 1. The dental camera 2 may be a handheld camera, for example, which measures the object 1 using a strip projection method. The strips may be coded using different light properties, such as intensity, color, polarization, coherence, phase, contrast, location and transit time. A confocal measurement method may also be used as the measurement method.

The individual images 3 are combined by means of a recording method to form a global image 5, wherein a check is performed automatically by computer 6 to ascertain whether the overlapping areas 7, which are represented with dashed lines, fulfill specific recording requirements for a correct recording. The recording requirements may include an adequate size of the overlapping areas 7, an adequate waviness of the object surface overlapping area, an adequate roughness of the surface overlapping area, an adequate number of characteristic geometries in the overlapping area 7, an adequate number of measuring points in the overlapping area 7 and/or an adequate image quality of the image 3 in the overlapping area. The third overlapping area 8 does not fulfill these recording requirements because the size of this overlapping area 8 is too small for successful recording. In such a case, a characteristic sound 10, which is represented by the radial lines, is generated as feedback for the user by means of a sound generator 9, which is arranged in the dental camera 2. Alternatively, a second sound is generated if the recording requirements are met. Alternatively or in addition to the first sound generator 9, a second sound generator 11 may also be arranged outside of the dental camera 2, for example, inside the computer 6 which produces a second characteristic sound 12. The sound 10, 12 may be optionally designed. The sound may be a characteristic clicking sound, for example, or a sound modulated in its tone pitch and/or its volume. During the measurement, additional individual images 3 may be recorded to form the global image 5, until the entire dental object 1 has been measured. The global image 5 can be displayed, for example, by means of a display device 13 such as means of a monitor, wherein input means 14 such as a mouse and a keyboard may be connected to the computer 6. The user can then rotate and shift the three-dimensional global image 5 by using the input means 14 and a cursor 15 to alter the direction of viewing.

Alternatively, the sound may be generated as a function of an object distance 16 between the dental camera 2 and the object 1 to be measured.

In another alternative, the sound may be generated as a function of the speed of movement of the dental camera 2 along the measurement path 4 relative to the object 1.

Figure 2:
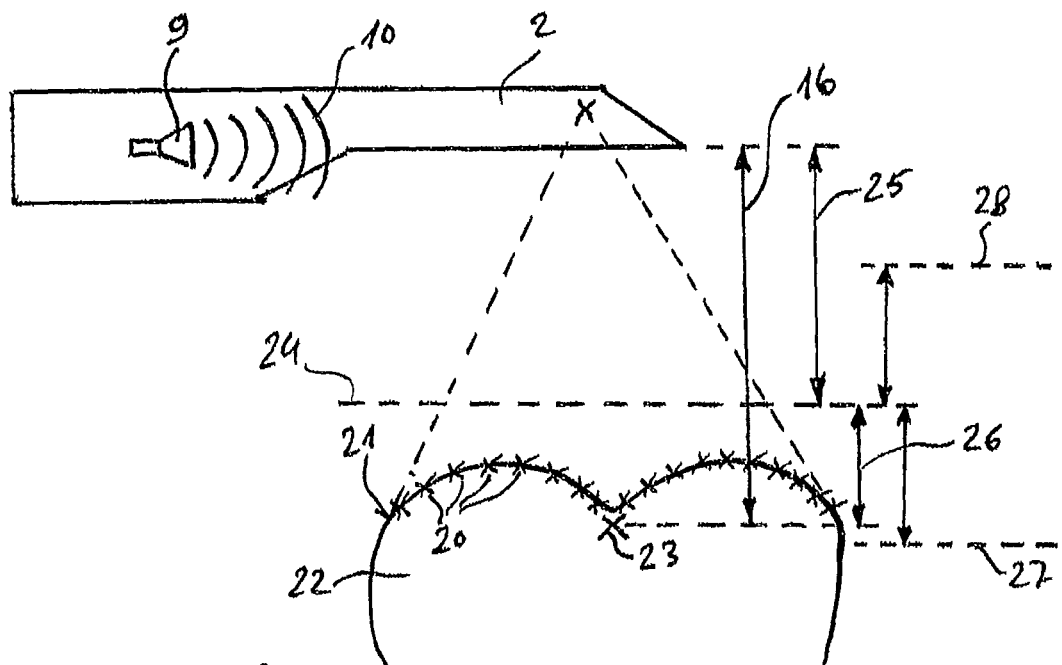
FIG. 2 a diagram illustrating the generating a sound as a function of an object distance.

FIG. 2 illustrates a diagram for clarification a characteristic sound 10 by means of the sound generator 9, which is integrated into the dental camera 2, as a function of the object distance 16. In the case presented here, the object distance 16 is determined by averaging the individual distances of the measuring points 20 on a defined occlusal surface 21 of a certain jaw tooth 22 relative to the dental camera 2, and a focal point 23, which is represented by a large X, is thereby calculated. The object distance 16 is thus the average distance between the dental camera 2 and the relevant object surface, such as an occlusal surface 21. The object distance may also be calculated by averaging all the measuring points within a measuring field. A focal plane 24 shows a known distance 25 from the dental camera 2, and this distance can be calculated by the pinhole camera model, taking into account the lens used. In the case of a strip projection method, the produced strips are sharply imaged in the focal plane. With knowledge of the specific object distance 16 and the known distance 25 from the focal plane, it is thus possible to calculate a focal distance 26 by subtraction. If this focal distance 26 exceeds a defined lower limit 27 or a defined upper limit 28, then the sound 10 is generated as a signal tone. The defined limits may be ±5 mm, for example. The sound 10 thus generated may also be a modulated sound, which is modulated in its tone pitch and/or volume, depending on the focal distance 26.

Figure 3:
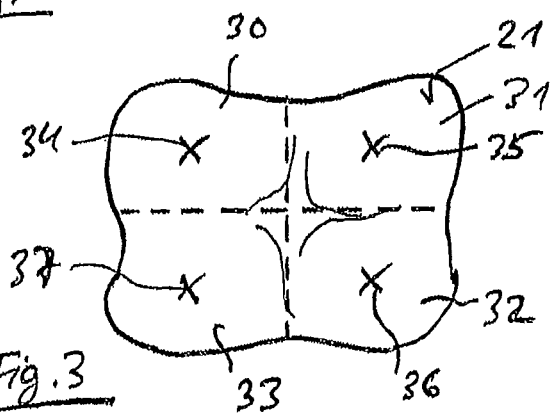
FIG. 3 a diagram illustrating an alternative embodiment for determining the object distance.

FIG. 3 illustrates a diagram for clarification an alternative embodiment for determining the object distance 16 from FIG. 2. The relevant occlusal area 21 is subdivided into four sectors 30, 31, 32, 33, wherein a first focal point 34, a second focal point 35, a third focal point 36 and a fourth focal point 37 are determined for each one of the sectors. Next, the distances of the respective focal points 34, 35, 36 and 37 are averaged relative to the camera 2, and the focal point of the total occlusal area 21 is thus determined.

Figure 4:
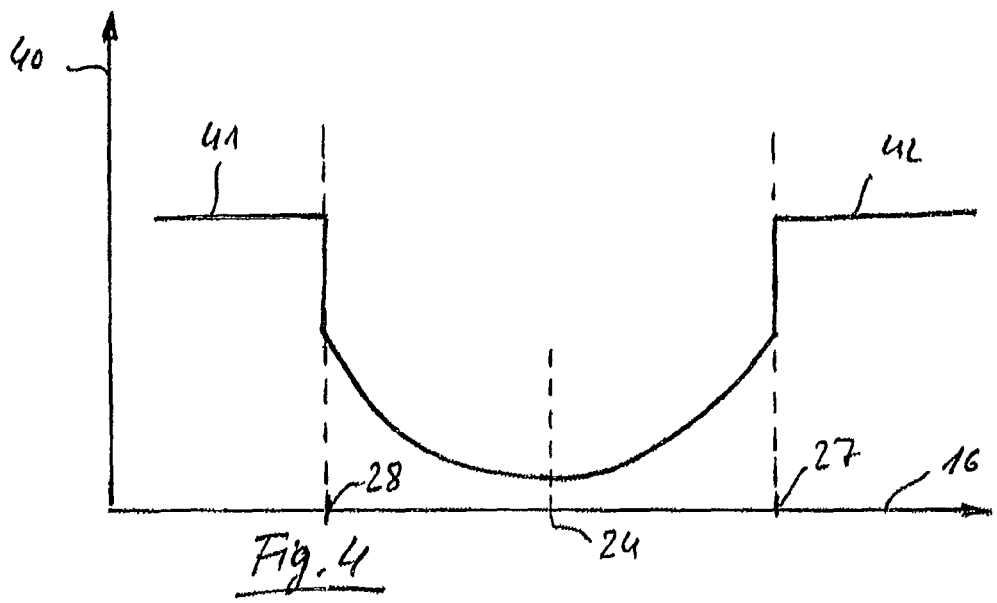
FIG. 4 a diagram for illustrating the generation of a modulated sound as a function of the object distance.

FIG. 4 illustrates a diagram for clarification, how a modulated sound is generated, wherein the graph shown represents the tone pitch and/or frequency of the sound 40 generated as a function of the object distance 16. The tone pitch of the sound is the lowest in the focal plane 24 and increases slowly up to the defined limits 27 and 28. On exceeding the limits 27 or 28, the tone pitch 40 increases suddenly into the regions 41 and 42, so that the dentist can discern clearly that the defined limits 27 or 28 have been exceeded.

Figure 5:
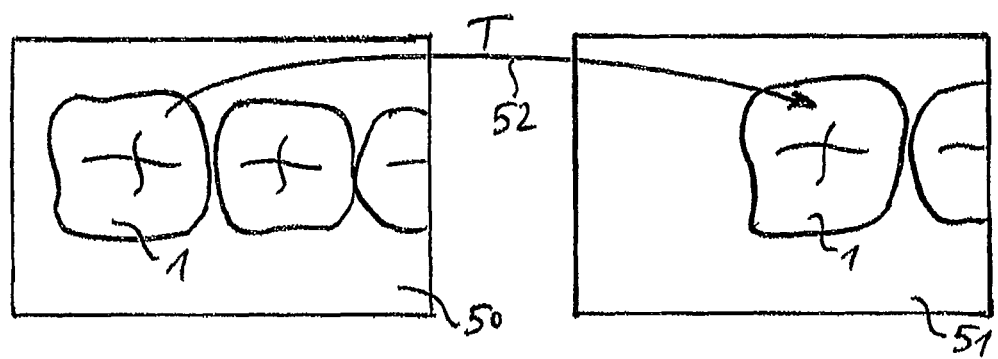
FIG. 5 a diagram illustrating the determination of the speed of movement on the basis of the images.

FIG. 5 illustrates a diagram for clarification, how the speed of movement of the dental camera 2 relative to the object 1 from FIG. 1 is determined by using an ICP algorithm. In a first image 50, a section of the object 1 is recorded, the dental camera 2 is moved along the measurement path 4 from FIG. 1 and a subsequent second image 51 is recorded, wherein the section of the object 1 has been shifted. Using the ICP algorithm, a translation 52, which may be a combination of a linear displacement and a rotation, is determined. Next, with knowledge of the image frequency and the determined translation 52, a speed of movement is determined for each of the measuring points on the object 1. Next, an average speed of movement is calculated by averaging the speed of movement of the individual measuring points. As soon as the critical speed of movement has been exceeded, the sound 10 from FIG. 1 can be generated to indicate to the dentist that he is moving the dental camera 2 too rapidly.

REFERENCE NUMERALS

1 Object
2 Camera
3 Image
4 Measurement path
5 Global image
6 Computer
7 Overlapping area
8 Overlapping area
9 Sound generator
10 Sound
11 Sound generator
12 Sound
12 Global image
14 Input mean
15 Cursor
16 Object distance
20 Measuring point
21 Occlusal surface
22 Jaw tooth
23 Focal point
24 Focal plane
25 Distance
26 Focal distance
27 Limit
28 Limit 30 Sector
31 Sector
32 Sector
33 Sector
34 Focal point
35 Focal point
36 Focal point
37 Focal point
40 Tone pitch
41 Region
42 Region
50 Image
51 Image
52 Translation

The invention claimed is:

1. A method of imaging a dental object using a dental camera comprising the steps of:
recording a plurality of three-dimensional optical images of a dental object using a dental camera;
determining whether an overlapping area, formed by at least a partial overlap of the plurality of three-dimensional optical images, satisfies one or more recording requirements; and
generating an acoustic sound during the recording using a sound generator;
wherein the sound serves as a feedback for the user and imparts to the user information (i) about the current status of a recording of the images and/or (ii) about recording requirements of the dental camera;
wherein a speed of movement of the dental camera relative to the object is determined by (i) using a motion sensor on the dental camera or (ii) by analysis of the measured images; and
wherein the acoustic sound is generated as a function of the determined speed of movement.

2. The method according to claim 1, wherein the sound generator emits a modulated sound, wherein the tone pitch and/or the volume of the sound can be changed depending on the speed of movement of the dental camera relative to the object.

3. The method according to claim 1, wherein the generated sound is a short clicking sound, which is generated as soon as a defined critical speed of movement is exceeded.

* * * * *